United States Patent [19]

Darfler

[11] Patent Number: 4,927,762

[45] Date of Patent: May 22, 1990

[54] CELL CULTURE MEDIUM WITH ANTIOXIDANT

[75] Inventor: Frederick J. Darfler, Derwood, Md.

[73] Assignee: Cell Enterprises, Inc., Harrisonburg, Va.

[21] Appl. No.: 281,974

[22] Filed: Nov. 30, 1988

Related U.S. Application Data

[63] Continuation of Ser. No. 846,716, Apr. 1, 1986, abandoned.

[51] Int. Cl.$^5$ .......................... C12N 5/00; C12N 5/02; C12N 1/38
[52] U.S. Cl. .............................. 435/240.31; 435/240.2; 435/240.25; 435/240.26; 435/240.3; 435/244
[58] Field of Search ............. 435/240.2, 240.26, 240.3, 435/240.31, 244, 240.25

[56] References Cited

PUBLICATIONS

Darfler et al., *J. Cell Phys.*, 115:31–36 (1983), "Clonal Growth of Lymphoid Cells in Serum-Free Media Requires Elimination of $H_2O_2$ Toxicity".

Broome et al., *J. Exp. Med.*, 138: 574–592 (1973), "Promotion of Replication in Lymphoid Cells by Specific Thiols and Disulfides in Vitro".

Primary Examiner—Charles F. Warren
Assistant Examiner—Gail Poulos
Attorney, Agent, or Firm—Iver P. Cooper

[57] ABSTRACT

Cells grown in chemically defined (serum free) media are protected against endogenous oxidizing agents by a nontoxic antioxidant with free thiol groups, at cell densities less than about $10^5$ cells/ml, especially DL-penicillamine, N-acetylcysteine, mercaptoproprionic acid, 2-mercaptoethanesulfonic acid, and thiolactate. These agents are useful in the maintenance and growth of hybridomas in such media.

26 Claims, No Drawings

CELL CULTURE MEDIUM WITH ANTIOXIDANT

This application is a continuation of Ser. No. 846,715, filed Apr. 1, 1986, now abandoned.

FIELD OF THE INVENTION

This invention relates to stabilization of chemically defined (serum free) media for hybridoma and lymphoid cell cultivation at low seed densities.

BACKGROUND OF THE INVENTION

Growth of hybridomas (immortalized antibody secreting cells) and lymphoid cells (immortal cells often used as fusion partners in constructing hybridomas) in serum-free media is very desirable. Serum is difficult and expensive to obtain, store and use; it is a source of undesirable foreign proteins which may be carried into the final product; its composition varies from lot to lot; and it is a potential source of contaminating organisms.

The present invention is concerned with culturing cells, in clouding mammalian cells, using a chemically-defined medium. The term "chemically-defined medium" is used in tissue culture to refer to culture media of known chemical composition, both quantitatively and qualitatively, in contrast to those media which contain natural products such as animal serum, embryo extracts, yeast hydrolysates, lactalbumin hydrolysates, tryptose or tryptone. In its strictest definition, it excludes high molecular weight proteins such as albumin which tightly bind other proteins and lipids which may resist purification.

A number of chemically-defined media are known. Most of these are solutions of carbohydrates, lipids, amino acids, vitamins, salts, minerals, purine and pyrimidine bases, etc. Some of these are widely used, for example, Dulbecco's modified Eagle's medium, In Vitro 6:89 (1970); Virology 8:396 (1959); Virology 12:185 (1960); Ham's F12 medium, Proc. Natl. Acad Sci. U.S.A. 63:288 (1965); In Vitro 6:89 (1970). Often one or more of these "basal media" are mixed in various proportions (e.g. Dulbecco's modified Eagle's medium: Ham's F12 medium, 1:1, vol:vol) before use, to obtain optimal growth for a given cell line.

Most basal media by themselves are ineffective at supporting the growth of most mammalian cells. The addition of supplemental factors, including transferrin, hydrocortisone, insulin, epidermal growth factor, ethanolamine, selenium and others is routinely required to obtain continuous growth of most mammalian cells in defined medium (Barnes and Sato, Anal. Biochem. 102:255 (1980)). Often the origin of the cell line under study dictates which supplements must be included to obtain optimal growth.

The formulation of defined media for the growth of lymphoid cells is commercially important for many reasons. Most established lymphoid cell lines secrete proteins, including interferons, interleukins, and antibodies, which have commercial applications. When the formulation of a defined medium for the growth of mammalian lymphoid cells was attempted, it was thought that serum albumin and 2-mercaptoethanol were necessary constituents in such preparations. More recently, it was discovered that catalase and dilinoleoyl phosphatidylcholine could replace albumin and 2-mercaptoethanol. Dilinoleoyl phosphotidylcholine supplied the requirement for an unsaturated fatty acid; catalase degraded harmful hydrogen peroxide that was present in basal tissue culture media. Also, it was learned that transferrin, selenium and ethanolamine were important for the growth of lymphoid cells in defined medium (Darfler and Insel, J. Cell. Physiol 115:31 (1983), Murakami et al, Anal. Biochem. 114:422 (1981), Iscove et al, Exp. Cell Res. 126:121 (1980), Chang et al, J. Immunol. Meth., 39:369 (1980)). Despite the progress in the development of defined media for lymphoid cells, many such preparations were unsatisfactory in that they displayed significant "dilution death", a term used to describe cell death resulting from diluting a culture of cells at high cell density (e.g. $1 \times 10^6$ cells/ml) to one of low cell density (less than $1 \times 10^3$ cells/ml).

As reported by McHugh, et al., BioTechniques, 72,76 (June/July 1983), hybridoma cells do not survive or grow well when plated at very low densities in serum free medium. Growth is particularly a problem in low density suspension cultures in serum-free media. Cleveland, et al., J. Immunol. Meth., 56:221 (1983).

While the inclusion of catalase in the medium offered some protection against dilution death, it was incompletely effective for certain cell lines using certain basal media; cloning efficiencies were 20% of maximum. Zigler et al (In Vitro Cell. and Dev. Biol. 21:282 (1985)) have shown that catalase was incompletely effective in protecting against toxicity due to media exposed to ordinary room light, suggesting the formation of toxic compounds that are not degraded by catalase. Similar results were reported by Wang and Nixon (In Vitro 14:715 (1978)).

Other groups (e.g. Kawamoto et al., Anal. Biochem. 130:445 (1985)) have attempted to overcome these problems by the inclusion of sulfhydryl-containing compounds such as 2-mercaptoethanol complexed to albumin; these two compounds together supplied reducing power to the medium. Similarly, cysteine has been used to supply the thiol requirement for serum-containing media (Broome and Jeng, J. Exp. Med. 138:574 (1973)). Cysteine, however, is less effective than 2-mercaptoethanol, probably owing to its more rapid degradation in tissue culture media.

Intensive efforts have been expended to discover formulations of serum-free media that are chemically-defined, stable, able to continuously grow lymphoid cells at clonal and high cell densities and which contain little or no high molecular weight proteins such as albumin.

Cartaya, U.S. Pat. No. Re. 30,985; Stemerman, U.S. Pat. No. 4,443,546 Torney, U.S. Pat. No. 3,887,403; and Weiss, U.S. Pat. No. 4,072,565 relate generally to serum-free media, which may contain the amino acids cysteine or cystine. Chang, et al., J. Immunol. Meth., 39:364–75 (1980) describe the growth of hybridomas in serum-free media. Murakami, et al., PNAS, 79:1158 (1982) report that ethanolamine was a necessary component of serum-free hybridoma growth media.

Darfler, et al., PNAS, 77:5993 (1980) described a new serum-free medium, containing casein, insulin, transferrin, testosterone, and linoleic acid, for growing murine lymphomas. They reported that 2-mercaptoethanol did not enhance growth in this "CITTL" medium. They later showed that CITTL was a medium suitable for the cultivation of a wide variety of transformed lymphoid cells, including hybridomas. Darfler and Insel, Exper. Cell Res., 138:287 (1982); Darfler and Insel, in Sato, ed., GROWTH OF CELLS IN NORMALLY DEFINED MEDIA, at 717 (1982).

Darfler and Insel, J. Cellular Physiol., 115:31 (1983) found that clonal growth of murine S49 T lymphoma cell lines required elimination of $H_2O_2$ toxicity, and used catalase as a scavenger for $H_2O_2$ in their serum-free medium.

Darfler, "In Vitro Immunization for the Generation of Hybridomas Using Serum-Free Medium", appearing in Bartal, ed., HYBRIDOMA FORMATION: MECHANISMS AND TECHNICAL ASPECTS OF HYBRIDOMA GENERATION AND MONOCLONAL ANTIBODY PRODUCTION (Humana Press, 1985) similarly overcame the problem of hybridoma susceptibility of hydrogen peroxide-mediated cytotoxicity. The growth medium included cysteine, but there was no teaching of any relationship of cysteine to inhibition of cytotoxicity. See also Darfler and Insel, in METHODS FOR SERUM-FREE CULTURE OF NEURAL AND LYMPHOID CELLS, 187 (1984).

Darfler and Insel showed that catalase can be used in serum-free tissue culture media for lymphoid cell growth to break down hydrogen peroxide to water and oxygen and prevent some of the damage of oxidizing, toxic agents. Catalase is less than satisfactory because it is a large (360,000 daltons) protein and, like albumin, its inclusion in tissue culture media hinders purification of proteins (e.g. antibodies) that are secreted by cultured lymphoid cells. Also catalase is incompletely effective at preventing damage to lymphoid cells in serum-free media when those cells are diluted to very low cell densities. Finally, catalase is potentially immunogenic and is unsuitable for use in tissue culture media intended for in vivo human uses and is less desirable for in vitro immunization protocols where levels of antigen may be in ng/ml levels.

Glutathione is known to play an important role in protecting cells against the destructive effects of reactive oxygen intermediates (such as $H_2O_2$) and free radicals. Tsan, et al., Biochem. & Brophys. Res. Commun., 127:270 (Feb. 28, 1985). Since cysteine is used for glutathione synthesis, inhibition of gamma-glutamylcysteine synthetase by buthionine sulfoximine depletes intracellular glutathione levels and may result in cell damage due to oxidants. Contrariwise, an intracellular cysteine delivery system may be used to promote glutathione synthesis and thus protect the cell. Williamson, PNAS, 79:6246 (1982); Wellner, PNAS 81:4732 (1984). Thor, et al., Arch. Biochem. Brophys., 192:405 (1979) reported that cysteine, N-acetylycysteine and methionine protect hepatocytes from bromobenzene toxicity by providing intracellular cysteine for gluthathione biosynthesis.

Wellner et al. showed that the inclusion of 5 mM reduced glutathione ester to a medium composed of RPMI 1640 plus fetal calf serum raised intracellular glutathione levels for up to 7 days and concomitantly protected human lymphoid cells from damage due to radiation. The effort to find such compounds that raise intracellular glutathione levels was for the purpose of using them for the detoxification of the liver and kidney. The glutathione ester described was readily susceptible to oxidation and hydrolysis and "appreciable oxidation" of the molecule occurs as well as "some cleavage of the ester group" under ordinary culture conditions. In a related study, Tsan et al showed that L-2-oxothiazolidine-4-carboxylate (a precursor of cysteine) can raise intracellular cysteine (and, hence, glutathione) levels in pulmonary artery endothelial cells. Levels of intracellular glutathione were less than 170% of control; when the cells were treated with hydrogen peroxide, only a slight protective effect on cell death resulted. L-2-oxothiazolidine-4-carboxylate contains no free sulfhydryl groups and, as a result, would not be expected to have any protective effects extracellularly against oxidizing, toxic agents. The use of L-2-oxothiazolidine-4-carboxylate as an inclusion to tissue culture medium has been suggested as a means to obviate the toxicity of cysteine in certain cells (Williamson et al., PNAS 79:6246 (1982)).

Taylor, "Toxicity and Hazards to Successful Culture: Cellular Responses To Damage Induced By Light, Oxygen Or Heavy Metals", appearing in Patterson, ed., USES AND STANDARDIZATION OF VERTEBRATE CELL CULTURE RESEARCH (Tissue Culture Association Monograph, No. 5, 1984), has reviewed the toxicity and hazards of cell culture, focusing on damage from light, oxygen and heavy metals. He summarizes those endogenous (in vivo) mechanisms which mitigate oxygen toxicity, including those mediated by pH, ceruloplasmin, transferrin, trace metals, superoxide dismutase, catalase, glutathione, glutathione peroxidase, vitamin E, cysteine and ascorbic acid. He proposed the "use of 'antioxidants', compounds that either terminate the chain of oxidative reactions or combine with free radicals to absorb and dissipate their energy nondestructively (quenchers, scavengers, et cetera)." Specifically, for in vitro cell culture, he suggests the use of 2-mercaptoethanol, butylated hydroxytoluene, butylated hydroxyanisole, ascorbic acid, sodium selenite, dimethlysulfoxide, dimethylurea and vitamin E.

Hoffeld reported that 2-mercaptoethanol enhances the availability of glutathione, and that glutathione then directly scavenges radicals and peroxides intracellularly. Eur. J. Immunol., 11:371 (1981); See also Hoffeld and Oppenheim, Eur. J. Immonol., 10:391 (1980).

Bernard et al., J. Clin. Invest., 73:1772 (1984) reported a study on the use of N-acetylcysteine in the treatment of adult respiratory distress syndrome. They hypothesized that oxygen free radicals are released in this disease and that intravenous N-acetylcysteine was effective at relieving the symptoms of these toxic radicals using an animal model system. In vitro studies were performed to show that N-acetylcysteine, in a dose-dependent manner, with optimal inhibition observed at 17 mM, inhibited the chemiluminescence generated by either phorbol ester-stimulated leukocytes or a cell-free hydrogen peroxide-generating enzyme system containing human plasma and albumin. They hypothesized that N-acetylcysteine is a "direct free radical scavenger." No suggestion was made of the use of N-acetylcysteine as an additive to chemically defined serum-free tissue culture media to prevent the toxicity of endogenously-generated oxidizing agents. Bernard taught use of NAC at a level (17 mM) over an order of magnitude higher than the level of NAC found to be toxic to lymphoid cells grown in vitro (1-2 mM) and found the levels taught herein (0.1-1.0 mM) to be only marginally effective for his application.

Ormstad and Ohno, Cancer Res., 44:3797 (1984) reported that increasing the urinary excretion of compounds containing free thiol groups, particularly N-acetylcysteine and sodium 2-mercaptoethane sulfonate (MESNA), protects against cyclophosphamide toxicity. Cyclophosphamide is used as a cytostatic agent in cancer chemotherapy and as an immunosuppressant in organ transplantation. MESNA was the preferred protective agent.

Broome and Jeng, J. Exper. Med., 138:574 (1973) reported that a number of thiols and disulfides may be substituted for L-cysteine in serum-containing media for L1210 murine lymphoid cells. Among others, 3-mercaptopropionate, 2-mercaptoethanol and dithiothreitol were found to be effective, whereas DL-p enicillamine was ineffective. In addition, L-cysteine was active whereas D-cysteine was not. Other lymphoma lines were found to respond differently to thiols-disulfides in vitro.

Kendall & Hutchins and Goodman & Weigle studied the effects of D-penicillamine (D-PEN) on the [3H]-thymidine incorporation of mouse splenic lymphocytes in serum-containing (both groups) and serum-free (Goodman and Weigle) media. Optimal levels of D-PEN were 3.35 mM (Kendall & Hutchins) and 1-8 mM (Goodman & Weigle). In serum-free medium, the optimal level was 1-3 mM. Both the oxidized and reduced forms of D-PEN were mitogenic when used alone, but only the reduced form was active in the presence of another mitogen such as lipopolysaccharide (Goodman and Weigle). Dithiothreitol was also active (Kendall and Hutchins). Kendall and Hutchins showed data to support their hypothesis that D-PEN improved the culture medium... "by assisting reduction of L-cystine to L-cysteine, which is taken up by some cells more readily than the oxidized form [cystine]..." See Kendall & Hutchins, Immunol., 35:189 (1978); Goodman & Weigle, Cell Immunol. 65: 337 (1981).

The cell concentrations used in the above studies were on the order of $10^6$ cells/ml. The toxic effects of oxidants are not usually evident until cell concentrations are reduced to $10^4$ cells/ml. The growth promoting substances of the present invention do not act by increasing cysteine uptake but rather by inactivating oxidizing agents. Kendall and Hutchins teach that dithiothreitol is effective, while I have found it ineffective at the lower cell densities contemplated by the present invention.

Claesson, et al., Med. Microbiol. Immunol., 167:161 (1979) found that D-Penicillamine had an enhancing effect on $^3$H-TdR uptake by human spleen cells in serum-containing media at concentrations of $10^{-3}$ to $10^{-2}$ moles. Human spleen cells did not survive serum-free conditions.

Immortal or immortalized cells are already "mitogen activated" and the mitogenic effect observed with D-Penicillamine is apparent only when it is administered to normal lymphocytes.

Saville, Analyst, 83:670 (1958) describes a scheme for the colorimetric determination of microgram amounts of thiols over 0.02 mM. This method can be used even in the presence of large amounts of amino acids and, as such, is suitable for assaying thiol levels in tissue culture media.

SUMMARY OF THE INVENTION

The present invention describes the use of penicillamine and N-acetylcysteine as protective agents that can be included in ordinary tissue culture media and are very effective at removing the toxicity due to oxidizing agents ordinary present in basal tissue culture media. Both agents were found to be effective in supporting the long-term growth of lymphoid cells, including hybridomas, even at low seed densities, when included in the serum-free, defined medium described below. Without limiting the invention to any theory of action, I would postulate that these agents destroy toxic, oxidizing activity in basal tissue culture media by two likely methods. These are: (1) a direct oxygen radical scavenging effect and, less likely, (2) the provision of a stable source of intracellular cysteine which also serves as a precursor to intracellular glutathione. Thor, et al, Acta Biophys. Biochem. 192:405 (1970). Elevated glutathione, in turn, provides protection against intracellular oxidative effects. The free sulfhydryl group is probably important in the direct oxygen radical scavenging ability of the molecule.

Other species which cannot serve as a raw material in glutathione biosynthesis have been discovered to be effective protective agents, probably by reason of direct scavenging.

Both penicillamine and N-acetylcysteine, unlike other antioxidant molecules such as 2-mercaptoethanol, do not have to be added complexed to albumin, thereby simplifying the purification of secretory proteins and eliminating a potential source of unknown molecules that may cling tightly to albumin.

Penicillamine and N-acetylcysteine are stable both at conditions of ordinary cell culture and in fully-reconstituted serum-free media which are routinely stored for extended periods at 4° C. prior to use. The deletion of albumin from such media may serve to stabilize N-acetylcysteine Ormstad and Ohno, Canc. Res. 44:3797 (1984). This group showed that the oxidation of N-acetylcysteine was hastened in human plasma (containing about 50% albumin) relative to Kreb's-Henseleit biocarbonate buffer using a carbogen (95% $O_2$, 5% $CO_2$) environment at 37° C. The half-life in plasma was approximately 2.3 hrs, whereas in plasma-free medium it was 5.4 hrs. More importantly, under conditions of ordinary cell culture, for example using 24-well tissue culture plates, N-acetylcysteine remains functionally active; the optimal concentration being 0.3 mM (Table IV). Under the same conditions cysteine is oxidized to cystine and readily precipitates, resulting in a slowing of cell growth and often cell death (Table I). Neither penicillamine nor N-acetylcysteine precipitates from tissue culture media under these conditions. The oxidation of N-acetylcysteine is hastened by the continuous presence of oxygen. However, in a tightly-sealed container of serum-free medium containing 0.3-1.0 mM N-acetylcysteine, the reducing power of the free sulfhydryl group of the molecule is maintained at high levels for over 4 weeks under conditions of ordinary storage (dark, 4° C.). More importantly, following storage for over 4 weeks at 4° C., penicillamine and N-acetylcysteine-containing, serum-free, defined medium described above are able to support the indefinite growth of hybridomas even at clonal densities. The half-life of 2-mercaptoethanol in albumin-free medium at 37° C. is 5.9 hrs (Broome and Jeng, J. Expp. Med. 138:574 (1973)). This is similar to the half-life of N-acetylcysteine. In addition, 2-mercaptoethanol in the presence of cystine has been proposed to form mixed disulfides which support the growth of human lymphoma cells (Ishii et al). In albumin-free medium, however, the addition of 2-mercaptoethanol (at 0.05-1.0 mmoles/liter) to a cystine-containing medium does not support the survival and growth of hybridoma cells (data not shown). The effectiveness of 2-mercaptoethanol, therefore is contingent upon the presence of albumin, unlike penicillamine or N-acetylcysteine.

The preferred compounds all have one or more free thiol groups imparting antioxidant activity. A "cell protective antioxidant" is a compound which when added to a medium, protects lymphoid and other cells from death attributable to oxidizing agents when the cells are seeded at low cell density in albumin-free, serum-free medium. It thus promotes cell growth under the conditions described in the legends to Tables I and IV when oxidizing agents are present. The preferred compounds, in descending order of effectiveness, were penicillamine, thiolactate, MPA, NAC and MESNA (See Table V). Cysteine, 2-mercaptoethanol and dithiothreitol have poor antioxidant activity at 0.05-1.0 mmoles/liter.

The ability to grow cells at low seed densities is desirable since cells grown in stationary culture at low seed density have metabolic activity indicative of that to be expected at high seed density in spinner culture (which increases exposure to oxidants), as might be employed in a production-scale process for the manufacture of a cell metabolite.

Also, in the development of hybridoma cell lines, the fused cells are diluted to extremely low cell densities (less than one cell per well), and are therefore particularly vulnerable to oxidizing agents.

The cell culture medium of the present invention is effective in promoting growth at seed densities at which oxidizing agents contribute significantly to cell death, typically concentrations of less than $10^5$ cells/ml. It should be noted that the critical cell density is related to the size of the cell, larger cells being more tolerant.

DETAILED DESCRIPTION OF THE INVENTION

Example 1

The efficacy of N-acetylcysteine to support the growth of hybridomas in serum-free medium was compared to that of two other agents, catalase and cysteine (Table I). Even at moderate cell densities, N-acetylcysteine promotes better growth than these two other compounds.

TABLE I

| Inclusion to medium | Cell number (cells/ml) |
|---|---|
| None | 131,200 |
| 5 ug/ml catalase | 151,500 |
| 1 mM cysteine | 120,400 |
| 1 mM N-acetylcysteine | 184,100 |

The mouse-human hybridoma LC2C12 was diluted into serum-free medium (described below) in the presence and absence of the above additions. After 5 days, cell number was assessed.

The medium of the invention is as follows: To a basal medium of RPMI 1640 or Dulbecco's modified Eagle's medium: Ham's F12 (1:1, vol:vol) was added to 0.1 to 1.0 mM penicillamine or N-acetylcysteine, 2-20 nM selenium dioxide or selenous acid, 1-30 ug/ml transferrin, 2-15 ug/ml insulin, 25-100 uM ethanolamine, 0.5-1.5 mg/ml beta-glycerophosphate , 0.3-2.0 ug/ml dilinoleoylphosphatidyl chlorine, and 1-2 mM glutamine. The optimal sodium bicarbonate concentration is 2.5 g/L for 8% $CO_2$ and 2.0 g/L for a 5% $CO_2$ environment

Example 2

That N-acetylcysteine acts via a mechanism distinct from the elevation of intracellular glutathione is shown by the following experiment. Hybridoma cells were diluted to low cell density in catalase-free, defined medium in the presence and absence of N-acetylcysteine. Also tested were the same cultures in the presence and absence of 50 uM L-buthionine-SR-sulfoximine, an inhibitor of gamma glutamylcysteine synthetase, hence preventing the formation of gluthathione from cysteine. Buthionine sulfoximine in the presence of N-acetylcysteine did not prevent N-acetylcysteine from protecting the cells from death due to toxic oxidants. This result shows that a significant portion of the protective effect of N-acetylcysteine is due to the direct free radical scavenging effect of the molecule. The results are shown in Table II below:

TABLE II

| Additive | Cell Number (Cells/ml) |
|---|---|
| None | 1280 |
| 50 uM buthionine sulfoximine | 1400 |
| 1 mM NAC | 3920 |
| Both | 3530 |

Thus, elevated levels of glutathione are not required for protection.

In another experiment, both L- and D- forms of penicillamine, which is structurally related to cysteine, were employed. Both forms were effective as shown in Table III below. Thus, the mechanism of action cannot depend on cysteine, gluthathione or protein synthesis as the D-form cannot serve as a biosynthetic precursor of these compounds.

TABLE III

| Additive | Low Seed Density | Moderate Seed Density |
|---|---|---|
| None | 930 cells/ml | 13,800 cells/ml |
| D-form | 2,430 | 34,200 |
| L-form | 2,660 | 37,400 |

Example 3

The effectiveness of N-acetylcysteine in improving lymphoid survival and growth when cultured in serum-free, albumin-free medium is dependent on the seed cell number (Table IV), as well as on the source of the basal medium used. A comparison of two medium preparations from separate suppliers showed that N-acetylcysteine was more effective for medium preparations which are more toxic without added N-acetylcysteine (Table IV). For a medium A, cell density improved survival and growth by 9%, whereas for the "poorer" medium B, the improvement from N-acetylcysteine was 36%. In contrast, at high cell densities, N-acetylcysteine at or above 0.3 mM is inhibitory to growth. These results suggest that N-acetylcysteine is not required exclusively in a nutritional sense, but acts to destroy toxic, oxidizing activity and, further, that levels of these toxic agents may vary considerably from preparation-to-preparation of basal media.

TABLE IV

| Inclusion to medium | Medium | Moderate seed density | High seed density |
|---|---|---|---|
| None | A | 19,200 | 203,300 |
| 0.3 mM N—acetyl cysteine (NAC) | A | 21,000 | 196,500 |
| 1.0 mM NAC | A | 19,300 | 204,000 |
| 2.0 mM NAC | A | 12,500 | 152,900 |
| None | B | 11,200 | 243,000 |
| 0.3 mM NAC | B | 15,200 | 221,300 |
| 1.0 mM NAC | B | 13,200 | 210,000 |
| 2.0 mM NAC | B | 8,000 | 151,000 |

The human-mouse hybridoma LC2C12 was incubated in the indicated serum-free media (prepared as in the legend to Table I) for 5 days. Compared are two basal media preparations (Dulbecco's modified Eagle's medium: Ham's F12 medium (1:1, vol:vol) from two suppliers (A and B). Example 4 improving growth at low cell density and did not inhibit cell growth at high cell density (92%).

Several structurally similar compounds have been found to be inactive:

| | |
|---|---|
| SH—CH$_2$—CH$_2$—OH | SH—CH$_2$—CH(SH)—CH$_2$—OH |
| 2-mercapto-ethanol | 2,3-dimercapto-1-propanol |
| (2ME) | (DMP) |
| SH—CH(CH$_3$)—CO—NH—CH$_2$—COO— | SH—CH$_2$—CH(OH)—CH$_2$—CH$_2$—SH |
| N-(2-mercapto-propionyl)-glycine | dithiothreitol |
| (MPG) | (DTT) |

The ability of N-acetylcysteine to remove the toxicity of oxidizing agents in serum-free medium for the culture of lymphoid cells suggests its use in an assay for levels of such oxidizing, toxic agents. For such an assay, lymphoid cells are cultured in the presence and absence of N-acetylcysteine (e.g. at 0.3 mM) as described in the legend to Table IV. The assay is designed to test basal media for these levels. Against the basal medium to be tested is run a basal medium known to be substantially free of toxic, oxidizing agents (e.g. medium A, Table IV). A sensitive lymphoid cell is cultured in serum-free media prepared from these basal media and relative cell numbers counted after 5 days gives an estimate of the levels of oxidizing, toxic material in the basal preparation. The addition of N-acetylcysteine to the medium containing the oxidizing activity should remove most of this activity. This assay must be useful for lot-to-lot quality control of basal media intended for use in the culturing of both lymphoid and other mammalian cells in the presence and absence of serum.

In summary, all of the active compounds fall into the class of:

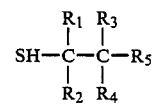

where $R_1$ and $R_2$ are H or $CH_3$, $R_3$ and $R_4$ are H, $NH_2$, or NH—CO—CH$_3$ or together form =O, and $R_5$ is $COO^-$, $SO_3^-$ or $CH_2$—$SO_3^-$, or when $R_3$ and $R_4$ together form =O, $R_5$ is $O^-$.

Example 6

The ability of penicillamine-containing serum-free, defined medium to support the growth of hybridomas suggests its use in the large-scale culture of those cells for the production of monoclonal antibodies secreted by those cells. The murine hybridoma C3-124, Kearney and Kubagawa, J. Exp. Med., 155, 839 (1981), was adapted to growth in the serum-free medium described in the legend to Table 1 using 5 ug/ml transferrin, 0.5 uM DL-penicillamine, 5 ug/ml insulin, 20 nM SeO$_2$, 50 uM ethanolamine, 1.5 mg/ml beta glycerophosphate 0.5 ug/ml dilinoleoylphosphatidyl choline and 2 mM gluta-

Example 5

The following compounds have been found to support lymphoid cell survival or growth at low cell density in serum-free, albumin-free medium:

| | |
|---|---|
| SH—CH(CH$_3$)—COO— | SH—CH$_2$—CH—(NH—CO—CH$_3$)—COOH |
| thiolactate | N-acetylcysteine |
| SH—C(CH$_3$)$_2$—CH(NH$_2$)—COOH | |
| penicillamine | |
| SH—CH$_2$—CH$_2$—SO$_3$— | SH—CH$_2$—CH$_2$—COO— |
| 2-mercaptoethanesulfonic | mercaptopropionic |
| acid | acid |
| (MESNA) | (MPA) |

TABLE V

| Inclusion to medium | Low seed density | High seed density |
|---|---|---|
| None | 2010 cells/ml | 82300 cells/ml |
| 0.15 mM MESNA | 3,800 | 97,100 |
| 0.15 mM MESNA | 3,940 | 96,800 |
| 0.15 mM MPA | 4,590 | 93,600 |
| 0.50 mM MPA | 3,910 | 99,200 |
| 0.15 mM NAC | 4,100 | 98,900 |
| 0.50 mM NAC | 3,570 | 99,600 |
| 0.15 mM L-penicillamine | 4,550 | 103,100 |
| 0.50 mM L-penicillamine | 4,790 | 105,600 |

The mouse-human hybridoma LC2C12 was diluted into serum-free medium (described in the legend to Table I) in the presence and absence of the indicated reagents. After 5 days, cell number was assessed.

Penicillamine was the most active of the aforementioned compounds. Best growth of cells seeded both at low and high cell densities was obtained 0.5 mM L-penicillamine.

In a separate experiment, 0.5 mM thiolactate was as nearly effective (99%) as 0.5 mM D-penicillamine at mine in a DME:Ham's F12 basal medium. The hybridomas cultures were fed with serum-free medium until the serum concentration was negligible. Then, the cells were grown to 140 ml at 0.39 × 10$^6$ cells/ml, fed with 30 ml serum-free medium and placed in a 250 ml spinner "micro-carrier" spinner flask (Bellco) in a 5% CO$_2$ incubator with the stir rate set at 20 RPM. As the cell culture expanded, the cells were placed in successively larger spinner flasks. Table VI shows the cell number and culture volume as a function of time.

TABLE VI

| Time (days) | Cell Number | Culture Volume (L) |
|---|---|---|
| 0 | 5.46 × 10$^7$ | 0.17 |
| 2 | 1.91 × 10$^8$ | 1.15 |
| 4 | 4.10 × 10$^8$ | 2.15 |
| 6 | 1.02 × 10$^9$ | 4.00 |
| 8 | 1.85 × 10$^9$ | 5.20 |
| 9 | 3.20 × 10$^9$ | 5.20 |

On day nine the cell culture was centrifuged, the spent medium was concentrated to 500 ml and the monoclonal antibody was precipitated by the addition of 185 g ammonium sulfate, 4° C., 16 hr. After centrifugation and washing, the protein content of the precipitate was estimated to be 16 mg with over 80% purity of antibody. These results demonstrate the utility of using this low protein (10ug/ml) serum-free, albumin-free medium for the production of monoclonal antibodies in purified form.

I claim:

1. A chemically defined, serum free, albumin-free medium for maintenance or growth of immortal or immortalized cells which comprises a cell-growth promoting amount of a compound having one free thiol group, and which is capable of supporting the growth of immortal or immortalized cells at seed densities less than $10^5$ cells/ml.

2. The medium of claim 1 wherein the compound has the formula:

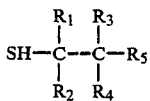

where $R_1$ and $R_2$ are H or $CH_3$, $R_3$ and $R_4$ are H, $NH_2$ or $NH(CO)CH_3$, and $R_5$ is $COO^-$, $SO_3^-$ or $CH_2SO_3^-$.

3. The medium of claim 1 wherein the compound does not have the structure HS—CHZ—CHK—Y where X is H or $NH_2$, Y is $COO^-$, and Z is H or $CH_3$.

4. The medium of claim 1 wherein the cell-growth-promoting amount is 0.1–1.0 mmoler/liter.

5. The medium of claim 1 wherein the compound is thiolactate.

6. The medium of claim 2 wherein the compound does not have the structure HS—CHZ—CHX—Y where X is H or $NH_2$, Y is $COO^-$, and Z is H or $CH_3$.

7. A chemically-defined, serum-free, medium for maintenance or growth of immortal or immortalized cells which comprises a cell growth promoting amount of a compound having one free thiol group, and which is capable of supporting the growth of immortal or immortalized cells at seed densities less than $10^5$ cells/ml.

8. The medium of claim 7 wherein the compound has the formula:

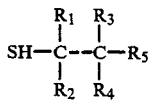

where $R_1$ and $R_2$ are H or $CH_3$, $R_3$ and $R_4$ are H, $NH_2$ or $NH(CO)CH_3$ and $R_5$ is $COO^-$, $SO_3^-$ or $CH_2$—$SO_3^-$.

9. The medium of claim 7 wherein the compound does not have the structure HS—CHZ—CHK—Y where X is H or $NH_2$, Y is $COO^-$, and Z is H or $CH_3$.

10. The medium of claim 7 wherein the cell-growth-promoting amount is 0.1–1.0 mmoles/liter.

11. The medium of claim 7 wherein the compound is thiolactate.

12. The medium of claim 8 wherein the compound does not have the structure HS—CHZ—CHX—Y where X is H or $NH_2$, Y is $COO^-$, and Z is H or $CH_3$.

13. A chemically defined, serum-free medium for the maintenance or growth of immortal or immortalized cells which comprises (a) a cell growth-promoting amount of a compound having one free thiol group, (b) insulin, and (c) transferrin, said medium being otherwise free of proteins.

14. A method of growing immortal or immortalized cells at seed densities less than $10^5$ cells/ml in a chemically defined serum-free medium which comprises inoculating a chemically defined, serum-free medium comprising a cell growth-promoting amount of a compound having one free thiol group with less than $10^5$ immortal or immortalized cells/ml medium and growing the cells in that medium.

15. The method of claim 14 in which the medium is also albumin-free.

16. The method of claim 14 in which insulin and transferrin are the sole protein components of the medium.

17. The method of claim 14 wherein the compound has the formula:

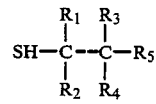

where $R_1$ and $R_2$ are H or $CH_3$, $R_3$ and $R_4$ are H, $NH_2$ or $NH(CO)CH_3$ and $R_5$ is $COO^-$, $SO_3^-$ or $CH_2SO_3^-$.

18. The method of claim 14 wherein the compound does not have the structure HS—CHZ—CHX—Y where X is H or $NH_2$, Y is $COO^-$, and Z is H or $CH_3$.

19. The method of claim 17 wherein the compound does not have the structure HS—CHZ—CHX—Y where X is H or $NH_2$, Y is $COO^-$, and Z is H or $CH_3$.

20. The method of claim 14 wherein the compound is thiolactate.

21. A supplemental cell culture medium consisting essentially of transferrin, insulin, ethanolamine, a selenium salt, an unsaturated fatty acid, and a cell-growth-promoting amount of a compound having one free thiol group, where said medium, when added to a basal cell culture medium, supports the growth of hybridoma cells at seed densities of less than $10^5$ cells/ml.

22. The method of claim 14 in which the cells are hybridoma cells.

23. The method of claim 14 wherein the compound is N-acetylcysteine.

24. The method of claim 14 wherein the compound is D- or L-penicillamine.

25. The method of claim 14 wherein the compound is MESNA.

26. The method of claim 15 wherein the compound is MPA.

* * * * *